(12) United States Patent
Nimmo et al.

(10) Patent No.: US 10,201,568 B2
(45) Date of Patent: *Feb. 12, 2019

(54) BRAIN, SPINAL, AND NERVE INJURY TREATMENT

(71) Applicant: EUSTRALIS PHARMACEUTICALS LIMITED, Adelaide, Pasedena (AU)

(72) Inventors: Alan John Nimmo, Townsville (AU); Robert Vink, Pasadena (AU)

(73) Assignee: EUSTRALIS PHARMACEUTICALS LIMITED, Melbourne, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/714,819

(22) Filed: Sep. 25, 2017

(65) Prior Publication Data

US 2018/0071333 A1 Mar. 15, 2018

Related U.S. Application Data

(60) Continuation of application No. 14/882,084, filed on Oct. 13, 2015, which is a continuation of application No. 12/475,627, filed on Jun. 1, 2009, now Pat. No. 9,186,404, which is a continuation of application No. 11/017,978, filed on Dec. 21, 2004, now abandoned, which is a division of application No. 10/181,323, filed as application No. PCT/AU01/00046 on Jan. 18, 2001, now Pat. No. 6,841,551.

(30) Foreign Application Priority Data

Jan. 18, 2000 (AU) ...................... PQ5146

(51) Int. Cl.
| | |
|---|---|
| *A61K 31/455* | (2006.01) |
| *A61K 31/495* | (2006.01) |
| *A61K 31/496* | (2006.01) |
| *A61K 31/44* | (2006.01) |
| *A61K 31/166* | (2006.01) |
| *A61K 33/06* | (2006.01) |
| *A61K 33/14* | (2006.01) |
| *A61K 45/06* | (2006.01) |
| *A61K 31/506* | (2006.01) |
| *A61K 31/5375* | (2006.01) |
| *A61K 31/5377* | (2006.01) |

(52) U.S. Cl.
CPC ............ *A61K 33/06* (2013.01); *A61K 31/455* (2013.01); *A61K 31/495* (2013.01); *A61K 31/496* (2013.01); *A61K 31/506* (2013.01); *A61K 31/5375* (2013.01); *A61K 31/5377* (2013.01); *A61K 33/14* (2013.01); *A61K 45/06* (2013.01); *A61K 31/166* (2013.01); *A61K 31/44* (2013.01); *Y10S 514/87* (2013.01)

(58) Field of Classification Search
CPC .. A61K 31/495; A61K 31/496; A61K 31/455; A61K 31/44

See application file for complete search history.

(56) References Cited

U.S. PATENT DOCUMENTS

| | | | |
|---|---|---|---|
| 4,481,139 | A | 11/1984 | Folkers et al. |
| 4,981,744 | A | 1/1991 | Swank |
| 4,985,896 | A | 1/1991 | Kimizuka et al. |
| 5,610,165 | A | 3/1997 | MacCoss et al. |
| 5,716,979 | A | 2/1998 | Horwell et al. |
| 5,744,482 | A | 4/1998 | Cohen et al. |
| 5,977,104 | A | 11/1999 | Baker et al. |
| 5,981,520 | A | 11/1999 | Shue et al. |
| 5,990,125 | A | 11/1999 | Howard |
| 5,998,444 | A | 12/1999 | Russell |
| 6,376,507 | B1 | 4/2002 | Nelson et al. |
| 6,479,483 | B2 | 11/2002 | Bos et al. |
| 6,841,551 | B2 | 1/2005 | Nimmo et al. |
| 9,186,404 | B2 | 11/2015 | Nimmo et al. |
| 2005/0107380 | A1 | 5/2005 | Nimmo et al. |
| 2016/0030474 | A1 | 2/2016 | Nimmo et al. |

FOREIGN PATENT DOCUMENTS

| | | |
|---|---|---|
| EP | 0 721 778 A2 | 7/1996 |
| EP | 1 035 115 A1 | 9/2000 |
| WO | 1997/038701 A1 | 10/1997 |
| WO | 1999/009987 A1 | 3/1999 |
| WO | 1999/064009 A1 | 12/1999 |
| WO | 2000/050398 A2 | 8/2000 |
| WO | 2000/050401 A1 | 8/2000 |
| WO | 2000/053572 A1 | 9/2000 |
| WO | 2000/073278 A1 | 12/2000 |
| WO | 2000/073279 A1 | 12/2000 |
| WO | 2001/025219 A1 | 4/2001 |

(Continued)

OTHER PUBLICATIONS

Haddad et al. Scandinavian J of Trauma, 2012, Resuscitation & Emergency Med., 2012, vol. 20, No. 12, pp. 1-15.*
Altura et al. (1982) "The role of magnesium in etiology of strokes and cerbrovasospasm," Magnesium. vol. 1:277-291.
Arango et al. (2008) "Magnesium for Acute Traumatic Brain Injury," Cochrane Database Syst. Rev. 2008(4): CD005400. pp. 1-18.
Bareyre et al. (2000) "Postinjury treatment with magnesium chloride attenuates cortical damage after traumatic brain injury in rats," J. Neurotrauma. 17(11):1029-1039.

(Continued)

*Primary Examiner* — Samira J Jean-Louis
(74) *Attorney, Agent, or Firm* — Brian C. Trinque; Benjamin A. Vaughan; Lathrop Gage LLP

(57) ABSTRACT

A treatment for brain, spinal and nerve injury comprising use of a substance P receptor antagonist optionally in combination with a magnesium compound. There is also provided a formulation for use in this treatment comprising a substance P receptor antagonist and a magnesium compound.

3 Claims, 2 Drawing Sheets

(56) References Cited

FOREIGN PATENT DOCUMENTS

WO      2001/052844 A1     7/2001

OTHER PUBLICATIONS

Bian et al. (1996) "Substance P(NK-1) Receptor and Non-Peptide Antagonist," Chinese Journal of Pain Medicine. 2 (3):181-185.
Chemical Abstracts 127:145069 (1997).
Chemical Abstracts 132:202964 (1999).
Cumberbatch et al. (1998) "Reversal of behavioural and electrophysiological correlates of experimental peripheral neuropathy by the NK1 receptor antagonist GR205171 in rats," Neuropharmacology. 37:1535-1543.
Faragó et al. (1991) "Contractile and endothelium-dependent dilatory responses of cerebral arteries at various extracellular magnesium concentrations," J. Cereb. Blood Flow Metab. 11:161-164.
Feickert et al. (1999) "Severe head injury in children: impact of risk factors on outcome," J. Trauma vol. 47:33-38.
Ferrari (1998) "Migraine," Lancet. 351:1043-1052.
Heath et al. (1996) "Traumatic brain axonal injury produces sustained decline in intracellular free magnesium concentration," Brain Research. 738:150-153.
Heath et al. (1999) "Improved motor outcome in response to magnesium therapy received up to 24 hours after traumatic diffuse axonal brain injury in rats," J. Neurosurg. 90:504-509.
Heath et al. (1998) "Neuroprotective effects of MgSO4 and MgCl2 in closed head injury: a comparative phosphorus NMR study," J. Neurotrauma. 15:183-189.
Heath et al. (1999) "Optimization of magnesium therapy after severe diffuse axonal brain injury in rats," J. Pharmacol. Exp. Ther. 288:1311-1316.
Heath et al. (1996) "Brain intracellular free magnesium declines after impact-acceleration induced brain injury in rats," Neurosci. Res. Commun. 18:163-168.
Heath et al. (1997) "Magnesium sulphate improves neurologic outcome following severe closed head injury in rats," Neuroscience Letters. 228:175-178.
Kemp et al. (1999) "Assessment of the effects of endothelin-1 and magnesium sulphate on regional blood flows in conscious rats, by the coloured microsphere reference technique," Br J. Pharmacol. 126:621-626.
Kramer et al. (1997) "Magnesium-deficiency-enhanced post-ischemic myocardial injury is reduced by substance P receptor blockade," Journal of Molecular and Cellular Cardiology. 29:97-110.
McIntosh et al. (1988) "Magnesium deficiency exacerbates and pretreatment improves outcome following traumatic brain injury in rats: 31P magnetic resonance spectroscopy and behavioral studies," J. Neurotrauma. 5:17-31.
Morril et al. (1998) "Mg2+ modulates membrane sphingolipid and lipid second messenger levels in vascular smooth muscle cells," FEBS Lett. 440:167-171.
Moskowitz (1984) "The neurobiology of vascular head pain," Ann. Neurol. 16:157-168.
Shepheard et al. (1995) "Comparison of the effects of sumatriptan and the NK1 antagonist CP-99,994 on plasma extravasation in Dura mater and c-fos mRNA expression in trigeminal nucleus caudalis of rats," Neuropharmacology. 34(3):255-261.
Temkin et al. (2007) Magnesium sulfate for neuroprotection after traumatic brain injury: a randomised controlled trial, Lancet Neural. 6:29-38.
Vink et al. (2001) "An overview of new and novel pharmacotherapies for use in traumatic brain injury," Clinical and Experimental Pharmacology and Physiology. 28(11):919-921.
Vink et al. (1988) "Decline in intracellular free Mg2+ is associated with irreversible tissue injury after brain trauma," J. Biol. Chem. 263:757-761.
Vink et al. (1996) "Acute and prolonged alterations in brain free magnesium following fluid percussion-induced brain trauma in rats," J. Neurochem. 66:2477-2483.
Vink et al. (1990) "Pharmacological and physiological effects of magnesium on experimental traumatic brain injury," Magnesium Res. 3:163-169.
Weglicki et al. (1997) "Neuropeptides, Free Radical Stress and Antioxidants in Models of Mg-Deficient Cardiomyopathy," In; Magnesium: Current Status and New Developments. Eds.: Theophanides et al. Kluwer Academic Publishers. pp. 169-178.
International Search Report corresponding to International Patent Application No. PCT/AU2001/000046, dated Apr. 24, 2001.
International Preliminary Report on Patentability corresponding to International Patent Application No. PCT/AU2001/000046, completed May 23, 2002.

\* cited by examiner

BRAIN, SPINAL, AND NERVE INJURY TREATMENT

PRIORITY TO RELATED APPLICATIONS

This application is a continuation of U.S. patent application Ser. No. 14/882,084, filed Oct. 13, 2015, now pending, which is a continuation of U.S. patent application Ser. No. 12/475,627, filed Jun. 1, 2009, now U.S. Pat. No. 9,186,404, issued Nov. 17, 2015, which is a continuation of U.S. patent application Ser. No. 11/017,978, filed Dec. 21, 2004, now abandoned, which is a division of U.S. patent application Ser. No. 10/181,323, filed Oct. 15, 2002, now U.S. Pat. No. 6,841,551, issued Jan. 11, 2005, which is a § 371 of PCT/AU01/00046, filed Jan. 18, 2001, which claims priority to Australian Provisional Patent Application No. PQ 5146, filed Jan. 18, 2000. The entire contents of the above-identified applications are hereby incorporated by reference.

FIELD OF THE INVENTION

This invention relates to a method to a method of therapy of brain, spinal and nerve injury. There is also provided a formulation which is particularly useful in the method.

Injury to the brain results in the development of motor and cognitive deficits that contribute to the significant morbidity experienced by survivors of brain injury. Moreover, it is an occurrence that has the highest incidence in younger members of society. Accordingly, injury to the brain is responsible for the greatest loss of productive life as compare to any other disease proves. Despite this, there is no effective therapy to improve outcome after brain injury. We disclose the use of a method of therapy as a robust pharmacologic intervention for the treatment of brain injury. Use of this therapy significantly improves both motor and cognitive outcome in mild to severe experimental brain injury and has also been found to have beneficial effect also for the treatment of spinal cord and nerve injuries.

BACKGROUND OF THE INVENTION

It is well known that brain injury results in the development of neurologic deficits through two mechanisms. The first of these is known as primary mechanisms. These occur at the time of the injurious even and include mechanical processes such as laceration, tearing, stretching and compression of verve fibers. Little can be done for this type of injury once it has occurred. The second mechanism is secondary injury, which includes biochemical and physiological processes, initiated by a primary injury but which manifest with time after the injury. It has been demonstrated that much of the morbidity after brain injury is associated with the development of this secondary injury. Give that the secondary injury develops from minutes to days after the primary event, there exists a window of opportunity to pharmacologically prevent this type of injury and significantly improve resultant outcome. However, the factors that make up secondary injury must first be identified and then "antifactors" developed to inhibit the injury process.

Our studies have concentrated on identifying secondary injury factors after brain injury and developing interventional therapies. One of the factors, that we have previously identified[1-4] as critical to determining outcome after injury, is brain magnesium ion concentration. This ion is a regulatory factor in a number of biochemical and physiological processes that are activated after brain injury. Indeed, a decrease in the magnesium ion concentration was observed to exacerbate the injury process while an increase in the concentration of magnesium ion was noted to attenuate the injury process and result in an improved outcome.[5] The treatment of brain injury with magnesium has since been shown to be effective.[1, 6-10] even when administered up to 24 hours after the primary event, and the success of the treatment in experimental animal studies has subsequently led to clinical trials in human brain injury.

Despite the attenuation of deficits after brain injury with magnesium administration, it was clear that there were still motor and cognitive deficits that persisted after the treatment. Our attention was particularly drawn to the fact that in younger animals, the accumulation of water in the brain (i.e. cerebral oedema or brain swelling) was still present and that this may present a significant risk factor. Indeed, in a recent clinical study,[11] delayed brain swelling was responsible for 50% of all deaths recorded in young victims of brain injury.

DESCRIPTION OF THE INVENTION

Figure 1:
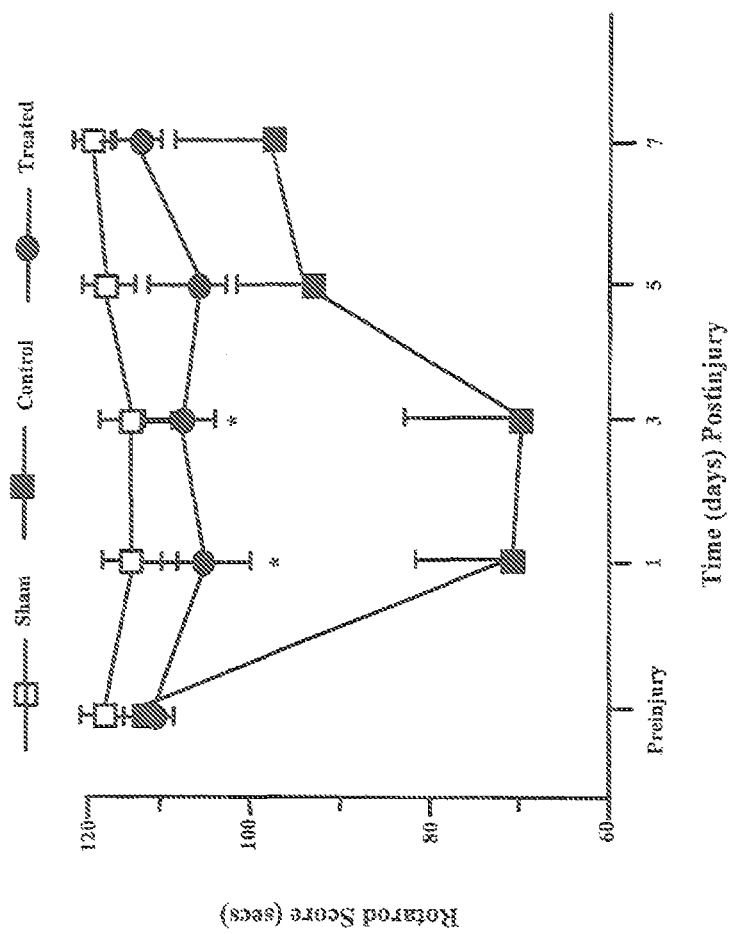
FIGS. 1 and 2 show combination administration of 246 mg/kg N-acetyl-L-tryptophan plus 30 mg/kg magnesium sulphate (intravenously) resulting in a profound attenuation of both motor and cognitive deficits that was significantly greater than obtained with either drug in isolation.

It therefore is an object of the invention to provide a method of therapy in relation to brain injury and a formulation for use in the method.

The formulation in one aspect of the invention comprises a substance P receptor antagonists and a magnesium compound, wherein the combined use of the magnesium compound and the substance P receptor antagonist results in greater protection against injury that either of the magnesium compound of the substance P receptor antagonist used alone.

The method of the invention includes the step of administering the formulation to a patient suffering from brain injury. Alternatively, each of the components of the formulation are administered separately or separated by a time delay that does not affect the effectiveness of the therapy, e.g. 1-30 minutes and up to 24 hours as discussed above.

Substance P is an excitatory neurotransmitter and has a role in pain transmission and is a peptide having the structure RPKPEEFFGLM-NH$_2$. It is from the hypothalamus, CSN and intestine and increases smooth muscle contraction of the GI tract.

It is known that substance P binds to a number of receptors inclusive of the NK1 receptor (i.e. Neurokinin 1 receptor), the NK2 receptor and the NK3 receptor. These receptors are believed to have a role in blood traveling to the brain.

Therefore, a substance P antagonist is a substance that inhibits binding of substance P to any one of the receptors referred to above. A list of suitable substance P antagonists is referred to in Tables 1, 2, and 3 attached herewith.

Reference may also be made to NK1 receptor antagonists as described in U.S. Pat. No. 5,990,125, which is incorporated herein by reference, as constituting substance P antagonists that may be utilized in the formulation of the method of the invention. This has specific reference to compounds of structures Ia, Ib, Ic, Id, Ie, X, XVI, XVII, XVIII, XIX, XX, and XXI, as well as other antagonists comprising quinuclidine, piperidine ethylene diamine, pyrrolidine and azabornane derivatives and related compounds that exhibit activity as substance P receptor antagonists as described in column 33 of U.S. Pat. No. 5,990,125.

Such receptor antagonists may be employed having regard to the dosages referred to in column 34 of U.S. Pat. No. 4,990,125 and in various forms of administration i.e. alone or with various pharmaceutically acceptable carriers or diluents by oral administration of parenteral administration as referred in column 34 of U.S. Pat. No. 5,990,125.

The activity of various substances as substance P receptor antagonists for use in the invention may also be determined by the assays referred to in columns 35-36 of U.S. Pat. No. 5,990,125.

Reference also may be made to substance P receptor antagonists described in U.S. Pat. No. 5,977,104, including the various dosage forms and dosages referred to in this reference which is also totally incorporated by reference.

Reference also is made to U.S. Pat. No. 4,481,139 that describes various peptide antagonists, which is also totally incorporated herein by reference.

Reference also is made to U.S. Pat. No. 4,985,896 which refers to various piperidine and morpholine derivatives for use as substance P antagonists for use in the present invention or piperazine derivatives as described in U.S. Pat. No. 5,981,520. Each of these references is totally incorporated herein by reference.

Reference also is made to piperidinyl compounds as NK1 and NK2 antagonists for use in the invention referred to in U.S. Pat. No. 5,998,444 which is also totally incorporated herein by reference.

It will also be appreciated that tachykinin antagonists referred to in U.S. Pat. No. 4,981,744 may also be used as substance P antagonists in the invention, and thus this reference is also totally incorporated herein.

Reference is also made to EP-A-1035115 which is totally incorporated herein by reference, which refers to N-benzyl-4-tolylnicotinamides and related compounds as NK1 receptor antagonists for use in the invention.

EP-A-1035115 discloses compounds of the general formula

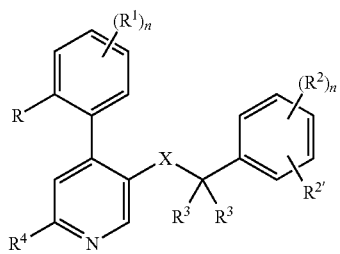

wherein
R is hydrogen, lower alkyl, lower alkoxy, halogen or trifluoromethyl;
R$^1$ is hydrogen or halogen;
R and R$^1$ may be together —CH=CH—CH=CH—;
R$^2$ and R$^{2'}$ are independently from each other hydrogen, halogen, trifluoromethyl, lower alkoxy or cyano; or
R$^2$ and R$^{2'}$ may be together —CH=CH—CH=CH—, optionally substituted by one or two substituents selected from lower alkyl or lower alkoxy;
R$^3$ is hydrogen, lower alkyl or form a cycloalkyl group;
R$^4$ is hydrogen, —N(R$^5$)$_2$, —N(R$^5$)(CH$_2$)$_n$(OH), —N(R$^5$)S(O)$_2$-lower alkyl, —N(R$^5$)S(O)$_2$-phenyl, —N=CH—N(R$^5$)$_2$, —N(R$^5$)C(O)R$^5$ or a cyclic tertiary amine of the group

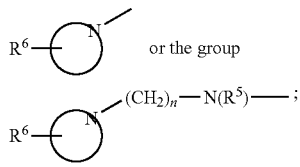

R$^5$ is, independently form each other, hydrogen, C$_{3-6}$-cycloalkyl, benzyl or lower alkyl;
R$^6$ is hydrogen, hydroxy, lower alkyl, —(CH$_2$)$_n$COO-lower alkyl, —N(R$^5$)CO-lower alkyl, hydroxy-lower alkyl, cyano, —(CH$_2$)$_n$O(CH$_2$)$_n$OH, —CHO or a 5- or 6 membered heterocyclic group, optionally bonded via an alkylene group,
X is —C(O)N(R$^5$)—; —(CH$_2$)$_m$O—; —(CH$_2$)$_m$N(R$^5$)—; —N(R$^5$)C(O)—; or —N(R$^5$)(CH$_2$)$_m$—; and
n is 0-4; and
m is 1 or 2;
and pharmaceutically acceptable acid addition salts thereof.

Exemplified compounds in EP-A-1035115 having a morpholine or piperazine group include
N-(3,5-Bis-trifluoromethyl-benzyl)-N-methyl-6-(4-methyl-piperazin-1-yl)-4-o-tolyl-nicotinamide,
2'-Methyl-5-(4-methyl-piperazin-1-yl)-biphenyl-2-carboxylic acid-(3,5-bis-trifluoromethyl-benzyl)-methyl-amide,
N-(3,5-Bis-trifluoromethyl-benzyl)-N-methyl-6-(4-methyl-piperazin-1-yl)-4-naphthalen-1-yl-nicotinamide,
(4-{5-[(3,5-Bis-trifluoromethyl-benzyl)-methyl-carbamoyl]-4-o-tolyl-pyridin-2-yl}-piperazin-1-yl)-acetic acid ethyl ester,
N-(3,5-Bis-trifluoromethyl-benzyl)-N-methyl-6-(4-propyl-piperazin-1-yl)-4-o-tolyl-nicotinamide,
N-(3,5-Bis-trifluoromethyl-benzyl)-N-methyl-6-[methyl-(2-morpholin-4-yl-ethyl)-amino]-4-o-tolyl-nicotinamide,
N-(3,5-Bis-trifluoromethyl-benzyl)-N-methyl-6-morpholin-4-yl-4-o-tolyl-nicotinamide,
N-(3,5-Bis-trifluoromethyl-benzyl)-N-methyl-6-piperazin-1-yl-4-o-tolyl-nicotinamide,
N-(3,5-Bis-trifluoromethyl-benzyl)-6-[4-(2-hydroxy-ethyl)-piperazin-1-yl]-N-methyl-4-o-tolyl-nicotinamide,
N-(3,5-Bis-trifluoromethyl-benzyl)-6-(4-cyanomethyl-piperazin-1-yl)-N-methyl-4-o-tolyl-nicotinamide,
N-(3,5-Bis-trifluoromethyl-benzyl)-6-{4-[2-(2-hydroxy-ethoxy)-ethyl]-piperazin-1-yl}-N-methyl-4-o-tolyl-nicotinamide,
N-(3,5-Bis-trifluoromethyl-benzyl)-N-methyl-6-(4-[1,2,4]oxadiazol-3-ylmethyl-piperazin-1-yl)-4-o-tolyl-nicotinamide,
N-(3,5-Bis-trifluoromethyl-benzyl)-N-methyl-6-[4-(5-oxo-4,5-dihydro-1H-[1,2,4]triazol-3-ylmethyl)-piperazin-1-yl]-4-o-tolyl-nicotinamide,
N-(3,5-Bis-trifluoromethyl-benzyl)-6-(4-formyl-piperazin-1-yl)-N-methyl-4-o-tolyl-nicotinamide,
N-Methyl-N-(2-methyl-naphthalen-1-ylmethyl)-6-morpholin-4-yl-4-o-tolyl-nicotinamide,
2-(3,5-Bis-trifluoromethyl-phenyl)-N-methyl-N-[6-(4-methyl-piperazin-1-yl)-4-o-tolyl-pyridin-3-yl]-isobutyramide,
2-(3,5-Bis-trifluoromethyl-phenyl)-N-[4-(2-chloro-phenyl)-6-(4-methyl-piperazin-1-yl)-pyridin-3-yl]-N-methyl-isobutyramide,
2-(3,5-Bis-trifluoromethyl-phenyl)-N-[4-(4-fluoro-2-methyl-phenyl)-6-(4-methyl-piperazin-1-yl)-pyridin-3-yl]-N-methyl-isobutyramide, 2-(3,5-Bis-trifluoromethyl-phenyl)-N-methyl-N-(6-morpholin-4-yl-4-o-tolyl-pyridin-3-yl)-isobutyramide,
2-(3,5-Bis-trifluoromethyl-phenyl)-N-[4-(2-chloro-phenyl)-6-morpholin-4-yl-pyridin-3-yl]-N-methyl-isobutyramide,
2-(3,5-Bis-trifluoromethyl-phenyl)-N-methyl-N-{6-[methyl-(2-morpholin-4-yl-ethyl)-amino]-4-o-tolyl-pyridin-3-yl}-isobutyramide,
2-(3,5-Bis-trifluoromethyl-phenyl)-N-methyl-N-[6-(4-pyrimidin-2-yl-piperazin-1-yl)-4-o-tolyl-pyridin-3-yl]-isobutyramide,
2-(3,5-Bis-trifluoromethyl-phenyl)-N-(6-morpholin-4-yl-4-o-tolyl-pyridin-3-yl)-isobutyramide,
2-(3,5-Bis-trifluoromethyl-phenyl)-N-methyl-N-(6-piperazin-1-yl-4-o-tolyl-pyridin-3-yl)-isobutyramide,
2-(3,5-Bis-trifluoromethyl-phenyl)-N-methyl-N-(6-morpholin-4-yl-4-o-tolyl-pyridin-3-yl)-acetamide and
[2-(3,5-Bis-trifluoromethyl-phenyl)-2-methyl-propyl]-[4-(4-fluoro-2-methyl-phenyl)-6-(4-methyl-piperazin-1-yl)-pyridin-3-yl]-methyl-amine.

Reference is also made to International Publication WO 0050398 which is totally incorporated herein by reference, which refers to various phenyl and pyridinyl derivatives as NK1 receptor antagonists for use in the invention.

WO 0050398 discloses compounds of general formula

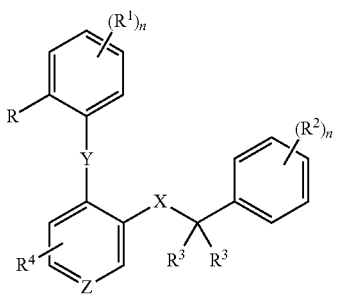

I wherein
R is hydrogen, lower alkyl, lower alkoxy, halogen or trifluoromethyl;
$R^1$ is hydrogen or halogen; or
R and $R^1$ may be together —CH=CH—CH=CH—;
$R^2$ is hydrogen, halogen, trifluoromethyl, lower alkoxy or cyano;
$R^3$ is independently from each other hydrogen, lower alkyl or form a cycloalkyl group;
$R^4$ is hydrogen, halogen, lower alkyl, lower alkoxy, —N($R^5$)$_2$, —N($R^5$)S(O)$_2$-lower alkyl, —N($R^5$)C(O)$R^5$ or a cyclic tertiary amine of the group

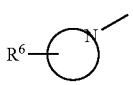

$R^5$ is, independently from each other, hydrogen, $C_{3-6}$-cycloalkyl, benzyl or lower alkyl;
$R^6$ is hydrogen, hydroxy, lower alkyl, —N($R^5$)CO-lower alkyl, hydroxy-lower alkyl, cyano, —CHO or a 5- or 6 membered heterocyclic group, optionally bonded via an alkylene group,
X is —C(O)N($R^5$)—, —(CH$_2$)$_m$O—, —(CH$_2$)$_m$N($R^5$)—, —N($R^5$)C(O)—, —C(O)O— or —N($R^5$)(CH$_2$)$_m$—;

Y is —(CH$_2$)$_n$—, —O—, —S—, —SO$_2$—, —C(O)— or —N($R^5$)—;
Z is =N—, —CH= or —C(Cl)=;
n is 0-4; and
m is 1 or 2;
and pharmaceutically acceptable acid addition salts thereof.

Exemplified compounds in WO 0050398 having a morpholine or piperazine group include
N-[2-Benzoyl-4-(4-methyl-piperazin-1-yl)-phenyl]-2-(3,5-bis-trifluoromethyl-phenyl)isobutyramide,
4-Benzoyl-N-(3,5-bis-trifluoromethyl-benzyl)-N-methyl-6-(4-methyl-piperazin-1-yl)-nicotinamide,
N-(3,5-Bis-trifluoromethyl-benzyl)-4-(2-chloro-benzoyl)-N-methyl-6-(4-methyl-piperazin-1-yl)nicotinamide,
N-(3,5-Bis-trifluoromethyl-benzyl)-N-methyl-6-morpholin-4-yl-4-phenoxy-nicotinamide,
N-(3,5-Bis-trifluoromethyl-benzyl)-4-(2-chloro-phenoxy)-N-methyl-6-morpholin-4-yl-nicotinamide,
N-(3,5-Bis-trifluoromethyl-benzyl)-4-(2-chloro-phenoxy)-N-methyl-6-(4-methyl-piperazin-1-yl)-nicotinamide and
N-(3,5-Bis-trifluoromethyl-benzyl)-N-methyl-6-morpholin-4-yl-4-o-tolyloxy-nicotinamide.

Reference is also made to International Publications WO 0050401, WO 0053572, WO 0073278 and WO 0073279, which refer to 3-phenyl pyridines, biphenyl derivatives, 5-phenyl-pyrimidine derivatives and 4-phenyl pyrimidine derivatives respectively which specifications are also totally incorporated herein by reference. These specifications refer to NK1 receptor antagonists for use in the present invention.

WO 0050401 discloses compounds of formula

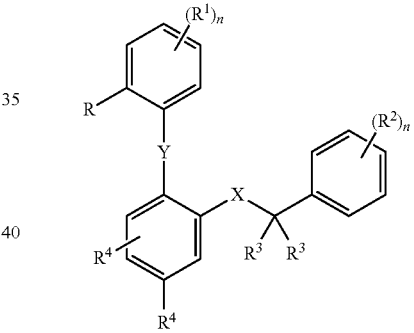

wherein
R is hydrogen, lower alkyl, lower alkoxy, halogen or trifluoromethyl;
$R^1$ is hydrogen or halogen; or
R and $R^1$ may be together —CH=CH—CH=CH—;
$R^2$ is hydrogen, halogen, trifluoromethyl, lower alkoxy or cyano;
$R^3$ is hydrogen, lower alkyl or form a cycloalkyl group;
$R^4$ is hydrogen, —N($R^5$)$_2$, —N($R^5$)S(O)$_2$-lower alkyl, —N($R^5$)C(O)$R^5$ or a cyclic tertiary amine of the group

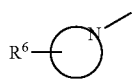

$R^5$ is, independently from each other, hydrogen, $C_{3-6}$-cycloalkyl, benzyl or lower alkyl;
$R^6$ is hydrogen, hydroxy, lower alkyl, —N($R^5$)CO-lower alkyl, hydroxy-lower alkyl, cyano, —CHO or a 5- or 6 membered heterocyclic group, optionally bonded via an alkylene group, X is —C(O)N(R⁵)—, —(CH₂)ₘO—, —(CH₂)ₘN(R⁵)—,
—N(R⁵)C(O)— or —N(R⁵)(CH₂)ₘ—;

n is 0-4; and m is 1 or 2;

and pharmaceutically acceptable acid addition salts thereof.

Exemplified compounds in WO 0050401 having a morpholine or piperazine group include N-(3,5-Bis-trifluoromethyl-benzyl)-5-(2-methoxy-phenyl)-N-methyl-2-(4-methyl-piperazin-1-yl)-isonicotinamide, N-(3,5-Bis-trifluoromethyl-benzyl)-N-methyl-2-(4-methyl-piperazin-1-yl)-5-phenyl-isonicotinamide, and N-(3,5-Dichloro-benzyl)-5-(2-methoxy-phenyl)-N-methyl-2-(4-methyl-piperazin-1-yl)-isonicotinamide.

WO 0053572 discloses compounds of formula

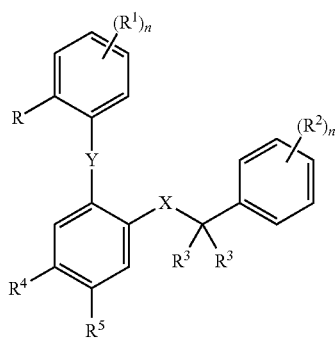

I wherein

R is hydrogen, lower alkyl, lower alkoxy, halogen, amino, —N(R⁶)₂ or trifluoromethyl;

R¹ is hydrogen, lower alkoxy or halogen;

R and R¹ may be together —CH=CH—CH=CH—;

R² is halogen, lower alkyl or trifluoromethyl;

R³ is hydrogen or lower alkyl;

R⁴ is hydrogen or a cyclic tertiary amine, optionally substituted by lower alkyl;

R⁵ is hydrogen, nitro, amino or —N(R⁶)₂;

R⁶ is hydrogen or lower alkyl;

X is —C(O)N(R⁶)—, —(CH₂)ₙO—, —(CH₂)ₙN(R⁶)—,
—N(R⁶)C(O)— or —N(R⁶)(CH₂)ₙ—; and n is 1 or 2;

and pharmaceutically acceptable acid addition salts thereof.

Exemplified compounds in WO 0053572 having a morpholine or piperazine group include 2'-methyl-5-(4-methyl-piperazin-1-yl)-biphenyl-2-carboxylic acid-(3,5-bis-trifluoromethyl-benzyl)-methyl-amide and 2'-chloro-5-(4-methyl-piperazin-1-yl)-biphenyl-2-carboxylic acid-(3,5-bis-trifluoromethyl-benzyl)-methyl-amide.

WO 0073278 discloses compounds of formula

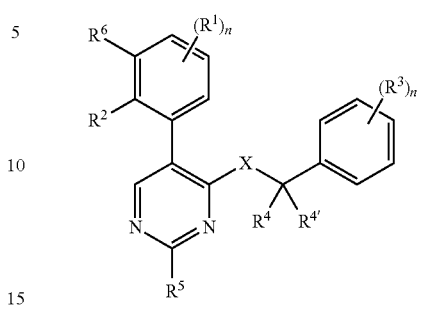

I wherein

R¹ is hydrogen or halogen;

R² is hydrogen, halogen, lower alkyl or lower alkoxy;

R³ is halogen, trifluoromethyl, lower alkoxy or lower alkyl;

R⁴/R⁴' are independently from each other hydrogen or lower alkyl;

R⁵ is lower alkyl, lower alkoxy, amino, hydroxy, hydroxy-lower alkyl, —(CH₂)ₙ-piperazinyl, optionally substituted by lower alkyl, —(CH₂)ₙ-morpholinyl, —(CH₂)ₙ₊₁-imidazolyl, —O—(CH₂)ₙ₊₁-morpholinyl, —O—(CH₂)ₙ₊₁-piperidinyl, lower alkyl-sulfanyl, lower alkyl-sulfonyl, benzylamino, —NH—(CH₂)ₙ₊₁N(R⁴″)₂, —(CH₂)ₙ—NH—(CH₂)ₙ₊₁N(R⁴″)₂, —(CH₂)ₙ₊₁N(R⁴″)₂, or —O—(CH₂)Fₙ₊₁N(R⁴″)₂, wherein R⁴″ is hydrogen or lower alkyl;

R⁶ is hydrogen;

R² and R⁶ or R¹ and R⁶ may be together with the two carbon ring atoms CH=CH—CH=CH—, with the proviso that n for R¹ is 1;

n is independently 0-2; and

X is —C(O)N(R⁴″)— or —N(R⁴″)C(O)—;

or pharmaceutically acceptable acid addition salts thereof.

Exemplified compounds in WO 0073278 having a morpholine or piperazine group include 5-(2-chloro-phenyl)-2-(4-methyl-piperazin-1-yl)-pyrimidine-4-carboxylic acid (3,5-bis-trifluoromethyl-benzyl)-methyl-amide, 5-(4-fluoro-2-methyl-phenyl)-2-(4-methyl-piperazin-1-yl)-pyrimidine-4-carboxylic acid (3,5-bis-trifluoromethyl-benzyl)-methyl-amide, 5-(2-chloro-phenyl)-2-(4-methyl-piperazin-1-ylmethyl)-pyrimidine-4-carboxylic acid (3,5-bis-trifluoromethyl-benzyl)-methyl-amide, 5-(2-chloro-phenyl)-2-(2-morpholin-4-yl-ethoxy)-pyrimidine-4-carboxylic acid (3,5-bis-trifluoromethyl-benzyl)-methyl-amide, 2-(3,5-bis-trifluoromethyl-phenyl)-N-methyl-N-[2-(4-methyl-piperazin-1-yl)-5-o-tolyl-pyrimidin-4-yl]-isobutyramide, 2-(3,5-bis-trifluoromethyl-phenyl)-N-methyl-N-(2-piperazin-1-yl-5-o-tolyl-pyrimidin-4-yl)-isobutyramide, 2-(3,5-bis-trifluoromethyl-phenyl)-N-methyl-N-(2-morpholin-4-yl-5-o-tolyl-pyrimidin-4-yl)-isobutyramide, and 2-(3,5-bis-trifluoromethyl-phenyl)-N-[5-(2-chloro-phenyl)-2-(4-methyl-piperazin-1-yl)-pyrimidin-4-yl]-N-methyl-isobutyramide.

WO 0073279 discloses compounds of formula

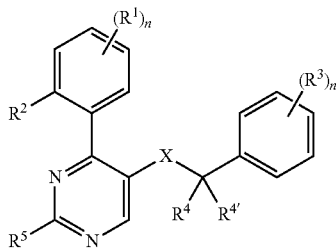

wherein
$R^1$ is hydrogen or halogen;
$R^2$ is hydrogen, halogen, lower alkyl or lower alkoxy;
$R^1$ and $R^2$ may be together with the two carbon ring atoms —CH=CH—CH=CH—;
$R^3$ is halogen, trifluoromethyl, lower alkyl or lower alkoxy;
$R^4/R^{4'}$ are independently from each other hydrogen or lower alkyl;
$R^5$ is lower alkyl, lower alkoxy, amino, phenyl, hydroxy-lower alkyl, cyano-lower alkyl, carbamoyl-lower alkyl, pyridyl, pyrimidyl, —$(CH_2)_n$-piperazinyl, lh is optionally substituted by one or two lower alkyl groups or by hydroxy-lower alkyl, —$(CH_2)_n$-morpholinyl, —$(CH_2)_n$-piperidinyl, —$(CH_2)_{n+1}$-imidazolyl, lower alkyl-sulfanyl, lower alkyl-sulfonyl, benzylamino, —NH—$(CH_2)_{n+1}$N$(R^{4''})_2$, —$(CH_2)_{n+1}$N$(R^{4''})_2$, —O—$(CH_2)_{n+1}$-morpholinyl, —O—$(CH_2)_{n+1}$-piperidinyl or —O—$(CH_2)_{n+1}$N$(R^{4''})_2$, wherein $R^{4''}$ is hydrogen or lower alkyl; and
n is 0-2;
X is —C(O)N($R^{4''}$)— or —N($R^{4''}$)C(O)—;
and pharmaceutically acceptable acid addition salts thereof.

Exemplified compounds in WO 0073279 having a morpholine or piperazine group include
4-(2-bromo-phenyl)-2-(4-methyl-piperazin-1-yl)-pyrimidine-5-carboxylic acid (3,5-bis-trifluoromethyl-benzyl)-methyl-amide,
(3R,5S)-4-(2-bromo-phenyl)-2-(3,5-dimethyl-piperazin-1-yl)-pyrimidine-5-carboxylic acid (3,5-bis-trifluoromethyl-benzyl)-methyl-amide,
4-(2-bromo-phenyl)-2-piperazin-1-yl-pyrimidine-5-carboxylic acid (3,5-bis-trifluoromethyl-benzyl)-methyl-amide,
4-(2-chloro-phenyl)-2-(4-methyl-piperazin-1-yl)-pyrimidine-5-carboxylic acid (3,5-bis-trifluoromethyl-benzyl)-methyl-amide,
(3R,5S)-4-(2-chloro-phenyl)-2-(3,5-dimethyl-piperazin-1-yl)-pyrimidine-5-carboxylic acid (3,5-bis-trifluoromethyl-benzyl)-methyl-amide,
4-(2-chloro-phenyl)-2-piperazin-1-yl-pyrimidine-5-carboxylic acid (3,5-bis-trifluoromethyl-benzyl)-methyl-amide,
2-(4-methyl-piperazin-1-yl)-4-o-tolyl-pyrimidine-5-carboxylic acid (3,5-bis-trifluoromethyl-benzyl)-methyl-amide,
(3R,5S)-2-(3,5-dimethyl-piperazin-1-yl)-4-o-tolyl-pyrimidine-5-carboxylic acid (3,5-bis-trifluoromethyl-benzyl)-methyl-amide,
2-piperazin-1-yl-4-o-tolyl-pyrimidine-5-carboxylic acid (3,5-bis-trifluoromethyl-benzyl)-methyl-amide,
4-(2-methoxy-phenyl)-2-(4-methyl-piperazin-1-yl)-pyrimidine-5-carboxylic acid (3,5-bis-trifluoromethyl-benzyl)-methyl-amide,
(3R,5S)-2-(3,5-dimethyl-piperazin-1-yl)-4-(2-methoxy-phenyl)-pyrimidine-5-carboxylic acid (3,5-bis-trifluoromethyl-benzyl)-methyl-amide,
4-(2-methoxy-phenyl)-2-piperazin-1-yl-pyrimidine-5-carboxylic acid (3,5-bis-trifluoromethyl-benzyl)-methyl-amide,
4-(4-fluoro-phenyl)-2-(4-methyl-piperazin-1-yl)-pyrimidine-5-carboxylic acid (3,5-bis-trifluoromethyl-benzyl)-methyl-amide,
4-(2-fluoro-phenyl)-2-(4-methyl-piperazin-1-yl)-pyrimidine-5-carboxylic acid (3,5-bis-trifluoromethyl-benzyl)-methyl-amide,
(3R,5S)-2-(3,5-dimethyl-piperazin-1-yl)-4-(2-fluoro-phenyl)-pyrimidine-5-carboxylic acid (3,5-bis-trifluoromethyl-benzyl)-methyl-amide,
4-(4-fluor-phenyl)-2-piperazin-1-yl-pyrimidine-5-carboxylic acid (3,5-bis-trifluoromethyl-benzyl)-methyl-amide,
4-(4-fluoro-2-methyl-phenyl)-2-(4-methyl-piperazin-1-yl)-pyrimidine-5-carboxylic acid (3,5-bis-trifluoromethyl-benzyl)-methyl-amide,
(3R,5S)-2-(3,5-dimethyl-piperazin-1-yl)-4-(4-fluoro-2-methyl-phenyl)-pyrimidine-5-carboxylic acid (3,5-bis-trifluoromethyl-benzyl)-methyl-amide,
4-(4-fluor-2-methyl-phenyl)-2-piperazin-1-yl-pyrimidine-5-carboxylic acid (3,5-bis-trifluoromethyl-benzyl)-methyl-amide,
2-(4-methyl-piperazin-1-yl)-4-naphthalen-1-yl-pyrimidine-5-carboxylic acid (3,5-bis-trifluoromethyl-benzyl)-methyl-amide,
(3R,5S)-2-(3,5-dimethyl-piperazin-1-yl)-4-naphthalen-1-yl-pyrimidine-5-carboxylic acid (3,5-bis-trifluoromethyl-benzyl)-methyl-amide,
4-naphthalen-1-yl-2-piperazin-1-yl-pyrimidine-5-carboxylic acid (3,5-bis-trifluoromethyl-benzyl)-methyl-amide,
4-(2-bromo-phenyl)-2-morpholin-4-yl-pyrimidine-5-carboxylic acid (3,5-bis-trifluoromethyl-benzyl)-methyl-amide,
4-(2-chloro-phenyl)-2-morpholin-4-yl-pyrimidine-5-carboxylic acid (3,5-bis-trifluoromethyl-benzyl)-methyl-amide,
4-(2-chloro-phenyl)-2-(2-morpholin-4-yl-ethoxy)-pyrimidine-5-carboxylic acid (3,5-bis-trifluoromethyl-benzyl)-methyl-amide,
2-morpholin-4-yl-4-o-tolyl-pyrimidine-5-carboxylic acid (3,5-bis-trifluoromethyl-benzyl)-methyl-amide,
4-(2-methoxy-phenyl)-2-morpholin-4-yl-pyrimidine-5-carboxylic acid (3,5-bis-trifluoromethyl-benzyl)-methyl-amide,
4-(4-fluoro-2-methyl-phenyl)-2-morpholin-4-yl-pyrimidine-5-carboxylic acid (3,5-bis-trifluoromethyl-benzyl)-methyl-amide,
2-morpholin-4-yl-4-naphthalen-1-yl-pyrimidine-5-carboxylic acid (3,5-bis-trifluoromethyl-benzyl)-methyl-amide,
2-(3,5-bis-trifluoromethyl-phenyl)-N-methyl-N-[2-(4-methyl-piperazin-1-yl)-4-o-tolyl-pyrimidin-5-yl]-isobutyramide and
2-(3,5-bis-trifluoromethyl-phenyl)-N-methyl-N-(2-morpholin-4-yl-4-o-tolyl-pyrimidin-5-yl)-isobutyramide.

Reference also may be made to the reference the 1998 Sigma Catalogue and more particularly to pages 1194-1997 which describe modifications of substance P or substance P fragments, which may be used as substance P antagonists, for use in the invention. This publication is also totally incorporated herein by reference.

In relation to the magnesium compound, this may comprises any suitable source of magnesium ion such as magnesium chloride, magnesium sulphate, magnesium oxalate, magnesium gluconate or other non toxic magnesium salt.

The pharmaceutical preparations in accordance with this invention can in addition also contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances. Thus the term "comprising" used in the specification should be interpreted in this context. The dosage can vary within wide limits and can, of course, be fitted to the individual requirements in each particular case. In general, a dosage of 1 to 20000 mg per patient, preferable 10 to 5000 mg and more preferably 50 to 2000 mg of the substance P receptor antagonist should be appropriate.

In relation to the development of the inventive concept, it was established by the present inventors that one reasons for acute water accumulation in the brain after injury was the result of vasogenic oedema formation. This is caused by an increased permeability of the blood brain barrier thus permitting vascular proteins and water to enter the extracellular space in the brain and cause swelling. Few studies have examined how this increased blood brain barrier permeability contributes to the development of neurological deficits after injury, and no studies have investigated whether inhibition of brain swelling improves outcome. Studies of migraine[12, 13] have suggested that the vasculature of the dura matter (outer meningeal lawyer) becomes more permeable to vascular components as a result of substance P release. We therefore hypothesized that substance P may have a similar effect on the cerebral vasculature, where such an effect could lead to increased blood brain barrier permeability and vasogenic cerebral oedema. We further hypothesized that administration of a substance P receptor antagonist may prevent brain swelling and the development of delayed neurologic deficits after injury. This hypothesis was a result of our discovery referred to above, that water accumulated in the brain as a result of vasogenic oedema formation.

This, in another aspect of the invention there is provided the use of a substance P receptor antagonist for reducing brain barrier permeability and/or vasogenic cerebral oedema.

EXPERIMENTAL

A number of commercially synthesized substance P receptor antagonists are currently available from standard scientific chemical suppliers, as is apparent form Tables 1, 2, and 3. We chose to use the compound N-acetyl-L-tryptophan based on its low lipid solubility that limits its ability to naturally cross the blood brain barrier and the fact that it is relatively inexpensive. Administration of N-acetyl-L-tryptophan at an intravenous dose of 246 mg/kg (saline vehicle) given at 30 minutes after brain injury resulted in a significant improvement of cognitive outcome in brain injured animals as assessed by the Barnes Circular Maze. Similarly, there was a significant improvement in motor outcome of animals as assessed by the otarod test. These improvements in outcome were apparent at 24 hours after brain injury and persisted for the 14 day assessment period. Control (vehicle tested) animals had significantly worse neurologic outcome than treated animals at all time points tested.

Animals treated with N-acetyl-L-tryptophan had a significant reduction in brain water accumulation (i.e. cerebral oedema) at 24 hours after injury as compared to vehicle treated controls. This was consistent with the observation that N-acetyl-L-tryptophan reduced brain penetration of Evans blue at 5 hours after injury: the time associated with maximum blood brain barrier permeability and reduced vasogenic oedema formation. The fact that these effects were noted with a non-permeable formulation of the NK1 antagonist suggests that the effects were largely mediated by vascular receptors and not dependent upon central receptors.

Administration of N-acetyl-L-tryptophan at 24.6 mg/kg also significantly improved cognitive outcome of brain injured animals. However, the drug had less of a beneficial effect on motor outcome. Moreover, because there was also some residual cognitive and motor deficits noted in all treated animals, the beneficial effects of treatment with the NK1 antagonist were less apparent when injury of mild severity was induced as opposed to injury of a severe nature. This is a major limitation given that mild head injury has the greatest incidence in brain injury patients.

Combination Magnesium and N-Acetyl-L-Tryptophan

The most common form of brain injury is mild head injury. Guidelines to be introduced next year (2000) by the World Federation of Neurological Surgeons will recommend that all cases of minor head injury with any complications such as vomiting, nausea, loss of consciousness or amnesia MUST present to a hospital. This will place considerable pressure on the health system to adequately treat these individuals such that secondary injury does not develop any further. Currently, there is no such therapy.

Our results with N-acetyl-L-tryptophan suggest that this compound closes the blood brain barrier after head injury and reduces brain swelling or cerebral oedema. This is extremely important in young victims of head injury who are particularly vulnerable to delayed brain swelling. Furthermore, our results with magnesium therapy suggest that magnesium treatment is effective at reducing neurologic deficits not necessarily associated with increased blood brain permeability. We therefore propose that a combination of a substance P antagonist with a magnesium compound or salt will be a particularly effective therapy for the treatment of brain injury irrespective of severity.

Figure 2:
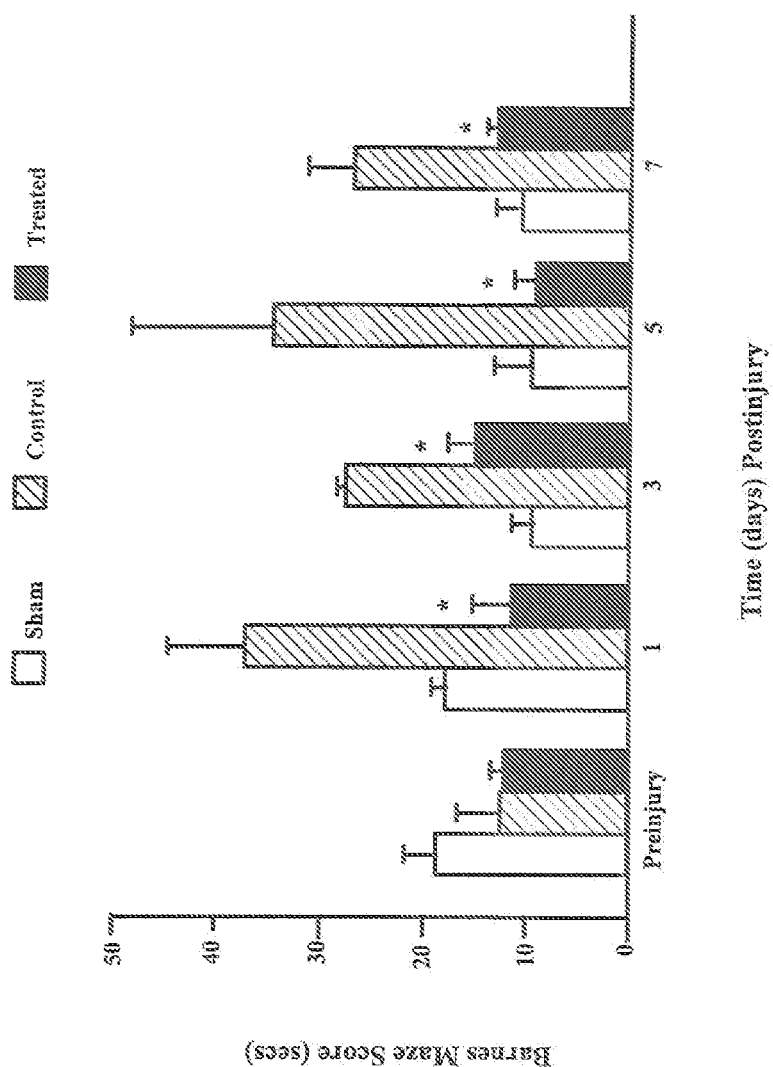

Combination administration of 246 mg/kg N-acetyl-L-tryptophan plus 30 mg/kg magnesium sulphate (intravenously) resulted in a profound attenuation of both motor and cognitive deficits that was significantly greater than obtained with either drug in isolation. (FIG. 1 and FIG. 2).

Each of the compounds in the combination formulation has a number of properties that make it particularly attractive for use in brain injury.

Substance P (SP) antagonists have been shown to rapidly improve mood by antagonizing substance P induced anxiety. Thus, they are effective in treating post-injury depression. From the word described above, it is apparent that SP antagonists reduce blood brain barrier permeability and inhibit the formation of vasogenic oedema and post-injury brain swelling or cerebral oedema. The antagonists also have been shown to inhibit pain. There are high numbers of substance P receptors in the hippocampus and striatum, those parts of the brain that are known to be associated with learning and memory. Inhibition of binding with SP antagonists may thus prevent substance P induced deficits in learning and memory. Our evidence presented above suggests that this may be the case. This has never been shown previously. Indeed, there has been no literature on the role of substance P, or any neuropeptides, in brain injury.

Magnesium affects over 300 cellular enzymes. It is not surprising; therefore, that magnesium has numerous targets at which it may improve outcome. These include, amongst others, blocking glutamate induced excitotoxicity, improving membrane stability and reducing the production of reactive oxygen species, improving energy status, inhibiting calcium channels, reducing neurotransmitter release, inhibiting mitochondrial transition pore opening, and inhibiting apoptosis. Notably, it also blocks glutamate induced release of substance P. Physiologically, magnesium has been shown (14-17) to improve cerebral blood flow, to reduce cerebral vasospasms, and to reduce vascular ceramide and prostaglandin production.

The combined use of magnesium and the substance P antagonist results in greater protection against neural injury than either drug used alone.

We have previously shown that magnesium has a beneficial effect in trauma when administered at intravenous doses ranging from 16 to 60 mg/kg. When administered as an intramuscular injection, the effective dose varies from 45 to 90 mg/kg. The target is to increase free magnesium concentration in the blood to approximately 1.0 mM, which is double the normal blood free magnesium concentration. Beneficial results are observed irrespective of the magnesium salt used.

Our studies with the substance P antagonist have demonstrated that the effective i.v. dose varies from 24.6 mg/kg to 240.6 mg/kg or higher, with the higher doses having a greater beneficial effect on motor outcome. Moreover, these doses pertain to antagonists that have low lipid solubility and thus limited blood brain barrier permeability. A highly lipid soluble formulation should exact the same beneficial actions; however, there may be centrally mediated side-effects that may be inappropriate.

When used in combination, the formulation may vary in the range described for the individual components. We have achieved excellent results using the maximum i.v. doses described for the individual components.

The combination magnesium/SP antagonist is expected to be useful in the following conditions:
- As a "first-aid" prophylactic treatment following traumatic brain injury
- As a "first aid" prophylactic treatment following minor head injuries, including concussion
- As a therapy following non-traumatic brain injuries, including stroke, hypoxia and any form of brain injury where oedema is implicated
- As a maintenance therapy following brain injury

REFERENCES

1. Vink R, McIntosh T K, Demediuk P, Weiner M W, Faden A I: Decline in intracellular free magnesium concentration is associated with irreversible tissue injury following brain trauma. *J Biol Chem* 263: 757-761, 1998
2. Vink R, Heath D L, McIntosh T K: Acute and prolonged alterations in brain free magnesium following fluid percussion induced brain trauma in rats. *J Neurochem* 66:2477-2483, 1996
3. Heath D L, Vink R: Brain intracellular free magnesium concentration declines following impact-acceleration induced brain injury in rats. *Neurosci Res Commun* 18: 163-168, 1996
4. Heath D L, Vink R: Traumatic brain axonal injury produces sustained decline in intracellular free magnesium concentration. *Brain Research* 738:15-153, 1996
5. McIntosh T K, Faden A I, Yamakami I, Vink R: Magnesium deficiency exacerbates and pretreatment improves outcome following traumatic brain injury in rats: 31P magnetic resonance spectroscopy and behavioral studies. *J Neurotrauma* 5:17-31, 1988
6. Vink R, McIntosh T K: Pharmacological and physiological effects of magnesium on experimental traumatic brain injury. *Magnesium Res* 3:163-169, 1990
7. Heath D L, Vink R: Magnesium sulphate improves neurologic outcome following severe closed head injury in rats. *Neuroscience Letters* 228:175-178, 1997
8. Heath, D L, Vink R: Neuroprotective effects of $MgSO_4$ and $MgCl_2$ in closed head injury: a comparative phosphorus NMR study. *J Neurotrauma* 15:183-189, 1998
9. Heath D L, Vink R: Delayed therapy with magnesium up to 24 hours following traumatic brain injury improves motor outcome. *J Neurosurg* 90:504-409, 1999
10. Heath D L, Vink R: Optimisation of magnesium therapy following severe diffuse axonal brain injury in rats. *J Pharmacol Exp Ther* 288:1311-1316, 1999
11. Feickert H G, Drommer S, Heyer R: Severe head injury in children: impact of risk factors. *J Trauma* 47:33-38, 1999
12. Moskkowitz M A: The neurobiology of vascular head pain. *Ann Neurol* 16: 157-168, 1984
13. Ferrari M D: Migraine. *Lancet* 351:1043-1052, 1998
14. Aktura B T, Altura B M: The role of magnesium in etiology of strokes and cerebrovasospasm. *Magnesium* 1: 277-291, 1982
15. Ferago M, Szabo C, Dora E, Horvath I, Kovach A G B: Contractile and endothelium-dependent dilatory responses of cerebral arteries at various extracellular magnesium concentration. *J Cereb Blood Flow Metab* 11:161-164, 1991
16. Kemp, P A, Gardiner S M, March J E, Rubin P C, Bennett T: Assessment of the effects of endothelin-1 and magnesium sulphate on regional blood flows in conscious rats, by the colour microsphere reference technique. *Br J Pharmacol* 126:621-626, 1999
17. Morril M A, Gupta R K, Kostellow A B, Gy M, Zhang, A, Altura B T, Altura B M: $Mg^{2+}$ modulates membrane sphingolipid and lipid second messenger levels in vascular smooth muscle cells. *FEBS Lett* 167-171, 1998

TABLE 1

NK1 RECEPTOR ANTAGONISTS

| Chemical Code | Chemical Name |
|---|---|
| CGP49823 | (2R,4S)-2-benzyl-1-(3,5-dimethylbenzoyl)-N-[(4-quinolinyl)methyl]-4-piperineamine) dihydrochloride |
| CP-96,345 | (2S,3S)-cis-(2(diphenylmethyl)-N-[(2-methoxyphenyl)methyl]-1-azabicyclo[2.2.2]octan-3-amine |
| CP-99,994 | ((2S,3S)-cis-3-(2-methoxybenzylamino)-2-phenyl-piperidine)dihydrochloride |
| CP-122,721 | (+)-(2S,3S)-3-(2-methoxy-5-trifluoromethoxybenzyl)amino-2-phenylpiperidine |
| FK 888 | N2-[(4R)-4-hydroxy-1-(1-methyl-1H-indol-3-yl)carbonyl-L-propyl\-N-methyl-N-phenylmethyl-L-3-(2-naphthyl)-alaninamide |
| GR203040 | (2S,3S and 2R,3R)-2-methoxy-5-tetrazol-1-yl-benzyl-(2-phenyl-piperidin-3-yl)amine |
| GR-205171 | 3-Piperidinamine,N-[[2-methoxy-5-[5-(trifluoromethyl)-1H-tetrazol-1-yl]phenyl]methyl]-2-phenyl-, (2S-cis) |
| GR 82334 | [D-Pro9]spiro-gamma-lactam]Leu10, Trp1]physalaemin-(1-11) |
| GR 94800 | PhCO-Ala-Ala-DTrp-Phe-DPro-Pro-Nle-NH2 |

TABLE 1-continued

NK1 RECEPTOR ANTAGONISTS

| Chemical Code | Chemical Name |
|---|---|
| HSP-117 | 3-Piperidinamine,N-[[2,3-dihydro-5-(1-methylethyl)-7-benzofuranyl]methyl]2-phenyl-, dihydrochloride, (2S-cis)- |
| L 703,606 | 1-Azabicyclo[2.2]octan-3-amine,2-(diphenylmethyl)-N-[(2-idophenyl)methyl]-, (2S-cis)-, oxalate |
| L 732,138 | N-acetyl-L-tryptophan |
| L 733,060 | ((2S,S)-3((3,5-bis(trifluoromethyl)phenyl)methyloxy)-2-phenyl piperidine |
| L 742,694 | (2-(S)-(3,5-bis(trifluoromethyl)benzyloxy)-3-(s)-phenyl-4-(5-(3-oxo-1,2,4-triazolo)methylmorpholine |
| L 754,030 | 2-(R)-(1-(R)-3,5-bis(trifluoromethyl)phenylethoxy)-3-(S)-(4-fluoro)phenyl-4-(3-oxo-1,2,4-triazol-5-yl)methylmorpholine |
| L 668,169 | L-Phenylalanine, N-[2-[3-[[N-[2-(3-amino-2-oxo-1-pyrrolidinyl)-4-methyl-1-oxopentyl]-L-methionyl-L-glutaminyl-D-tryptophyl-N-methyl-L-phenylalanyl]amino]-2-oxo-1-pyrrolidinyl]-4-methyl-1-oxopentyl]-L-methionyl-L-glutaminyl-D-tryptophyl-N-methyl-, cyclic (*->1)-peptide, [3R-[1[S[R*(S*)]],3R*]]- |
| LY 303241 | 1-Piperazineacetamide, N-[2-[acetyl[2-methoxyphenyl)methyl]amino]-1-(1H-indol-3-ylmethyl)(ethyl)-4-phenyl-, (R)- |
| LY 303870 | (R)-1-[N-(2-methoxybenzyl)acetylamino]-3-(1H-Indol-3-yl)-2-[N-(2-(4-(piperidinyl)piperidin-1-yl)acetyl)amino]propane |
| LY 306740 | 1-Piperazineacetamide, N-[2'-acetyl[(2-methoxyphenyl)methyl]amino]-1-(1H-indol-3-ylmethyl)ethyl]-4-cyclohexyl-, (R)- |
| MEN 11149 | 2-(2-naphthyl)-1-N-[(1R,2S)-2-N-[1(H)indol-3-ylcarbonyl]aminocyclohexanecarbonyl]-1-[N'-ethyl-N'-(4-methylphenylacetyl)]diaminoethane |
| MK-869 | 3H-1,2,4-Triazol-3-one, 5-[[2-[1-[3,5-bis(trifluoromethyl)phenyl]ethoxy]-3-(4-fluorophenyl)-4-morpholinyl]methyl]-1,2-dihydro-, [2R-[2α(R*),3α]]- |
| PD 154075 | (2-benzofuran)-CH$_2$OCO]-(R)-alpha-MeTrp-(S)-NHCH(CH$_3$)Ph |
| R-544 | Ac-Thr-D-Trp(FOR)-PHe-N-MeBzl |
| RP-67580 | (3aR,&aR)-7,7-diphenyl-2[1-imino-2(2-methoxyphenyl)-ethyl+++perhydroisoindol-4-one hydrochloride |
| RPR 100893 | (3aS,4S,7aS)-7,7-diphenyl-4-(2-methoxyphenyl)-2-[(S)-2-(2-methoxyphenyl)proprionyl]perhydroisoindol-4-ol |
| Spendide | Tyr-D-Phe-Phe-D-His-Leu-Met-NH$_2$ |
| Spantide II | D-NicLys1, 3-Pal3, D-Cl$_2$Phe5, Asn6, D-Trp7.0, Nle11-substance P |
| Spantide III | L-Norleucinamide, N6-(3-pyridinylcarbonyl)-D-lysyl-L-prolyl-3-(3-pyridinyl)-L-alanyl-L-prolyl-3,4-dichloro-D-phenylalanyl-L-asparaginyl-D-tryptophyl-L-phenylalanyl-3-(3-pyridinyl)-D-alanyl-L-leucyl- |
| SR140333 | (S)-1-[2-[3-(3,4-dichlorophenyl)-1-(3-isopropoxyphenylacetyl)-piperidin-3-yl]ethyl]-4-phenyl-1-azabicyclo[2.2.2]octane |
| WIN-41,708 | (17beta-hydroxy-17alpha-ethynyl-5alpha-androxtano[3,2-b]pyrimido[1,2-a]benzimidazole |
| WIN-62,577 | 1H-Benzimidazo[2,1-b]cyclopenta[5,6]naphtha[1,2-g]quinazolin-1-ol, 1-ethynyl-2,3,3a,3b,4,5,15,15a,15b,16,17,17a-dodecahydro-15a,17a-dimethyl-, (1R,3aS,3bR,15aR,15bS,17aS)- |

TABLE 2

NK2 RECEPTOR ANTAGONISTS

| Chemical Code | Chemical Name |
|---|---|
| SR-48,968 | (S)-N-methyl-N[4-(4-acetylamino-4-[phenylpiperidino]-2-(3,4-dichlorophenyl)-butyl)benzamide |
| L-659,877 | Cyclo[Gln,Trp,Phe,Gly,Leu,Met] |
| MEN 10627 | Cyclo(Met-Asp-Trp-Phe-Dap-Leu)cyclo(2beta05beta) |
| SR 144190 | (R)-3-(1-[2-(4-benzoyl-2-(3,4-difluorophenyl)-morpholin-2-yl)-ethyl]-4-phenylpiperidin-4-yl)-1-dimethylurea |
| GR 94800 | PhCO-Ala-Ala-D-Trp-Phe-D-Pro-Pro-Nle-NH$_2$ |

TABLE 3

NK3 RECEPTOR ANTAGONISTS

| Chemical Code | Chemical Name |
|---|---|
| SR-142,801 | (S)-(N)-(1-(3-(1-benzoyl-3-(3,4-dichlorophenyl)piperidin-3-yl)propyl)-4-phenylpiperidin-4-yl)-N-methyl acetamide |
| R820 | 3-indolylcarbonyl-Hyp-Phg-N(Me)-Bzl |
| R486 | H-Asp-Ser-Phe-Trp-beta-Ala-Leu-Met-NH$_2$ |
| SB222200 | (S)-(−)-N-(a-ethylbenzyl)-3-methyl-2-phenylquinoline-4-carboximide |
| L 758,298 | Phosphonic acid, [3-[[2-[1-[3,5-bis(trifluoromethyl)phenyl]ethoxy]-3-(4-fluorophenyl)-4-morpholinyl]methyl]-2,5-dihydro-5-oxo-1H-1,2,4-triazol-1-yl]-,[2R-[2α(R*),3α)]- |

TABLE 3-continued

NK3 RECEPTOR ANTAGONISTS

| Chemical Code | Chemical Name |
|---|---|
| NK-608 | (2R,4S)-N-[1-{3,5-bis(trifluoromethyl)-benzoyl}-2-(4-chloro-benzyl)-4-piperidinyl]-quinoline-4-carboxamide |

The invention claimed is:

1. A method of reducing brain swelling in a subject in need thereof comprising administering to a subject a therapeutically effective amount of a pharmaceutical preparation comprising a therapeutically effective amount of a substance P receptor antagonist selected from the group consisting of:
N-(3,5-Bis-trifluoromethyl-benzyl)-N-methyl-6-(4-methyl-piperazin-1-yl)-4-o-tolyl-nicotinamide:

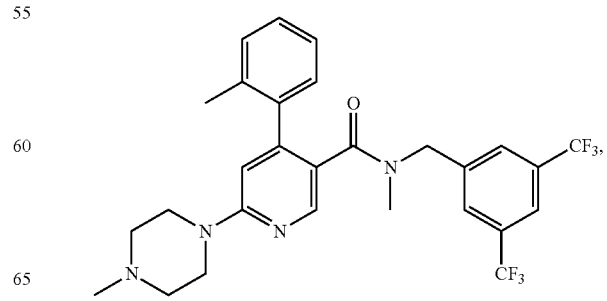

and
N-(3,5-Bis-trifluoromethyl-benzyl)-N-methyl-6-piperazin-1-yl-4-o-tolyl-nicotinamide:
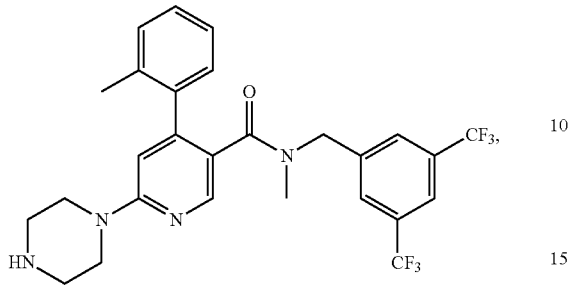
or a pharmaceutically acceptable salt thereof.
2. The method of claim 1, wherein the brain swelling is associated with a mechanical traumatic brain injury.
3. The method of claim 2, wherein the brain swelling is associated with stroke.
* * * * *